(12) United States Patent
Carlsson et al.

(10) Patent No.: US 6,547,770 B2
(45) Date of Patent: Apr. 15, 2003

(54) OPHTHALMIC DISPENSING DEVICE

(75) Inventors: Tony Carlsson, Hammarö (SE); Bengt Hedman, Karlstad (SE)

(73) Assignee: Aiolos Systems Aktiebolag (AB), Karlstad (SE)

( * ) Notice: Subject to any disclaimer, the term of this patent is extended or adjusted under 35 U.S.C. 154(b) by 0 days.

(21) Appl. No.: 09/834,195

(22) Filed: Apr. 12, 2001

(65) Prior Publication Data

US 2002/0004653 A1 Jan. 10, 2002

Related U.S. Application Data

(60) Provisional application No. 60/197,294, filed on Apr. 14, 2000.

(51) Int. Cl.[7] .................. A61M 35/00; A61M 37/00; B67D 5/42
(52) U.S. Cl. .................. 604/294; 604/295; 604/141; 222/387
(58) Field of Search .................. 604/294, 295, 604/296, 297, 298, 407, 408, 141, 147; 222/387, 402.16

(56) References Cited

U.S. PATENT DOCUMENTS

| | | | |
|---|---|---|---|
| 4,784,652 A | 11/1988 | Wikstrom | |
| 5,053,000 A | * 10/1991 | Booth et al. | 128/200.14 |
| 5,152,435 A | 10/1992 | Stand et al. | |
| 5,199,616 A | * 4/1993 | Martin | 222/402.16 |
| 5,207,659 A | * 5/1993 | Pennaneac'h et al. | 222/340 |
| 5,630,793 A | * 5/1997 | Rowe | 128/200.14 |
| 5,997,518 A | * 12/1999 | Laibovitz et al. | 604/296 |

* cited by examiner

Primary Examiner—Henry Bennett
Assistant Examiner—Alfred Basichas
(74) Attorney, Agent, or Firm—Alston & Bird LLP

(57) ABSTRACT

A manually operated dispensing device for delivering ophthalmic solution to the surface of an eye in a desired spray pattern with an impact pressure on the eye that is comfortably tolerated by an individual. The device comprises a pressure container having a closed bottom and an open top defining a neck, for accommodating a pressurized gas and a pouch; a sealed pouch, for the ophthalmic solution, made of a barrier material and exhibiting a valve which is integrated with a mounting cup adapted to fit the neck of the container; and an actuator adapted to fit the mounting cup of the sealed pouch, comprising a nozzle member including a cylindrical tube member, adapted to interact with the valve, and an actuator button for activating the interaction between the nozzle member and the valve, in order to accomplish said desired spray pattern.

19 Claims, 3 Drawing Sheets

OPHTHALMIC DISPENSING DEVICE

CROSS-REFERENCE TO RELATED APPLICATION

Figure 1:
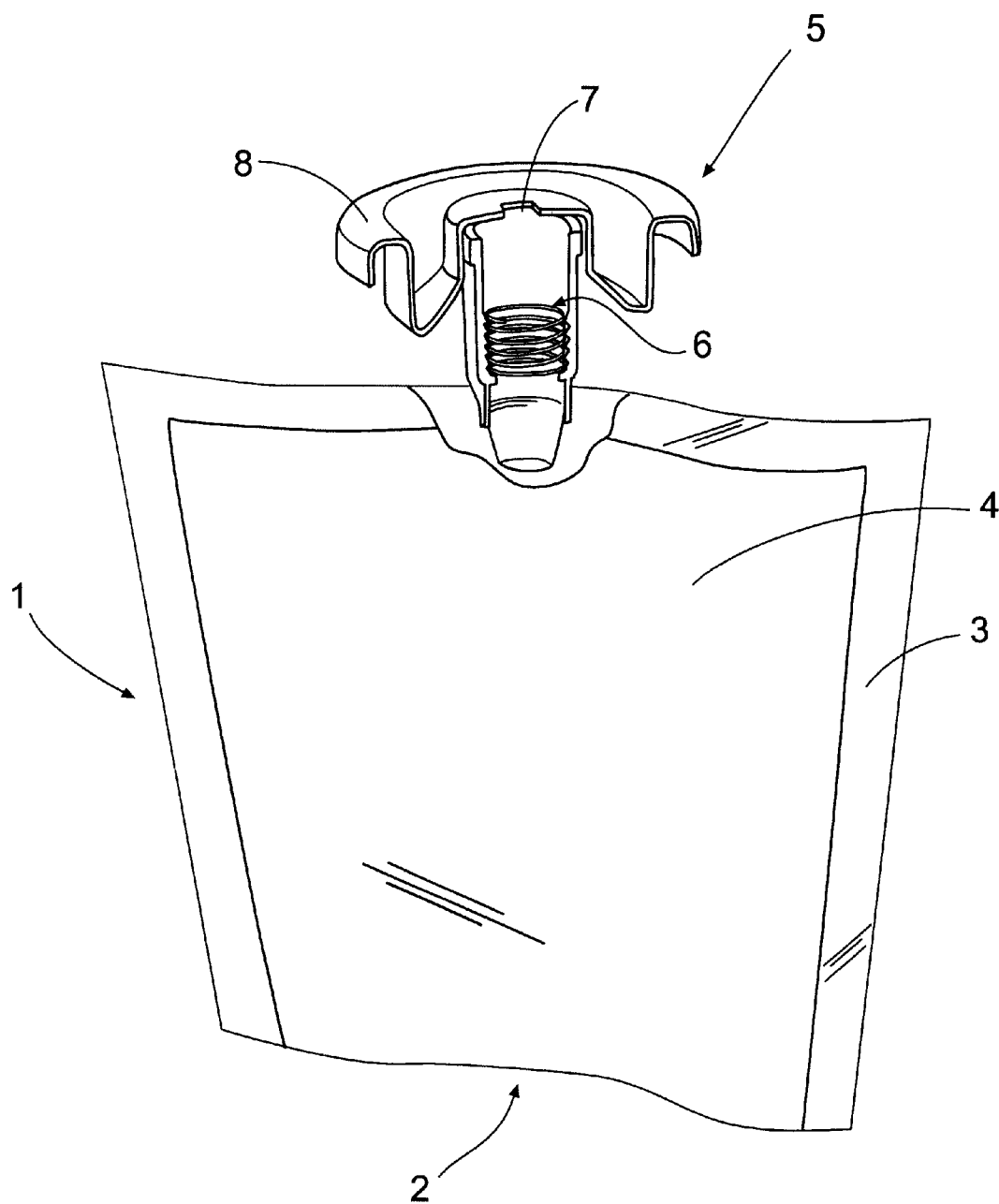

The present application claims the benefit of the filing date of U.S. Provisional Patent Application 60/197,294, filed Apr. 14, 2000, which is incorporated herein by reference.

BACKGROUND OF THE INVENTION

The present invention relates to a manually operated dispensing device for delivering ophthalmic solution to the surface of an eye in a desired spray pattern with an impact pressure on the eye that is comfortably tolerated by an individual.

Traditionally, eye wash with an ophthalmic solution such as an isotone (0.9%) solution of sodium chloride, have been performed by pouring a relatively large amount of solution into the eye. The solution is conventionally maintained in a flexible container, the sealing of which is broken when the solution is to be used. Thereafter, the flexible container is held above the contaminated eye and the container is squeezed to allow a flow of solution into the eye. Although the result most often is good, the eye being adequately rinsed, the method suffers from a number of drawbacks. The amount of solution which flows out of the flexible container when it is squeezed is undesirably high, resulting in a loss of solution and an undesirable wetting of clothes etc. In this regard an excess of solution used does not improve the rinsing of the eye. Also, a certain free space is required above the eyes of the individual to be treated, in order for the container to be held above the eyes. Moreover, each container can only be used once since, when the seal has been broken, the sterilization of the solution remaining in the container is destroyed.

In U.S. Pat. No. 5,152,435 there is shown a manually operated dispensing pump intended to provide a precise quantity of ophthalmic solution to the surface of an eye in a desired spray pattern with an impact pressure on the eye that is comfortably tolerable by an individual. By the pump, the solution is pumped from a nonpressurized container. Although the object of the pump as shown is to provide a desired diverging spray pattern with a low impact pressure, it has been found that the spray flow from a manually operated pump, operatively connected to a nonpressurized container, is difficult to control. The resulting spray flow depends too much on the person using the pump, which means that too weak a press or too hard a press on the actuator button will result in undesired flow properties, such as spray pattern, droplet size and impact pressure, in the flow which is produced. Moreover, when the pump has not been used for some time, the actuator button must be pressed down a number of times before solution has been transported through the pipe all the way up to the nozzle. This means that the delivery of solution takes some time, time which may be crucial for the recovery of the eye.

From SE 451 295 there is known another device for delivering ophthalmic solution to the surface of an eye. The device exhibits a container for the solution which container also contains a drive gas capsule. When the device is to be used, the capsule is penetrated and the drive gas is brought to expand inside a rubber pouch. By the expansion of the rubber pouch, the solution is brought to form a spray flow via a nozzle. The device has at least the drawbacks that it can only be used once, and that instructions are needed in order for the individual to understand how to use the device. It is easy to understand that an individual who has received chemical or physical contamination in the eyes, cannot read information on the device, which means that there is a risk of misuse of the device, leading to a fatal result for the eyes.

For other types of dispensing devices, such as nose sprays, shaving foam, cosmetic sprays, etc., it is known to use a "bag-in-can" concept in order to achieve a pressurized dispensing device without the use of halogenated compounds in the drive gas. The "bag-in-can" concept includes a pressure container having a closed bottom and an open top defining a neck, for accommodating a pressurized gas and a sealed, flexible pouch. The pouch, which accordingly is accommodated inside the container is made of an essentially diffusion proof barrier material and exhibits a valve which is integrated with a mounting cup adapted to fit the neck of the container. When the container is to be filled with liquid and drive gas, the drive gas is filled into the container first. Thereafter, the open neck of the container is sealed by the mounting cup being crimped onto the neck of the container. Now, the liquid is filled into the pouch via the valve in the mounting cup, so that a desired total pressure is achieved inside the pouch/container. Although the "bag-in-can" concept has been known for some time, it has not been suggested to use the concept in connection with a manually operated dispensing device for delivering ophthalmic solution to the surface of an eye.

None of the above identified prior art devices is directed to a manually operated dispensing device for delivering ophthalmic solution to the surface of an eye, which device can be used to deliver the solution in a desired non-excessive spray pattern, with a desired impact pressure and a desired droplet size, very soon after an eye contamination has occurred, without the need of special instructions for the use of the device, and which device can be used over and over again while retaining the sterilization of the solution.

Therefore, it is a primary object of the present invention to provide a manually operated pressurized dispensing device for delivering ophthalmic solution to the surface of an eye, very soon after an eye contamination has occurred, without the need of special instructions for the use of the device, and which can be operated from any position.

It is a further object of the present invention to provide a manually operated pressurized dispensing device for delivering ophthalmic solution to the surface of an eye, in a desired non-excessive spray pattern, with a desired impact pressure and desired droplet size.

It is a further object of the present invention to provide a manually operated pressurized dispensing device for delivering ophthalmic solution to the surface of an eye, which device can be used over and over again while retaining the sterilization of the solution.

SUMMARY OF THE INVENTION

The manually operated dispensing device of the present invention is provided for delivering ophthalmic solution to the surface of an eye, in a desired non-excessive spray pattern, with a desired impact pressure and desired droplet size, very soon after an eye contamination has occurred, without the need of special instructions for the use of the device, over and over again while retaining the sterilization of the solution.

The device according to the invention comprises a pressure container having a closed bottom and an open top defining a neck, for accommodating a pressurized gas and a pouch; a sealed pouch, for the ophthalmic solution, made of a barrier material and exhibiting a valve which is integrated with a mounting cup adapted to fit the neck of the container;

and an actuator adapted to fit the mounting cup of the sealed pouch, comprising a nozzle member including a cylindrical tube member, adapted to interact with the valve, and an actuator button for activating the interaction between the nozzle member and the valve, in order to accomplish the desired spray pattern.

The nozzle member of the present pressurized dispensing device is designed to give the desired non-excessive spray pattern, with a desired impact pressure and a desired droplet size. Especially, this is achieved by the design of the cylindrical tube member, which exhibits a venturi passageway including a nozzle outlet which creates a conical spray pattern which diverges at an angle $\alpha$ in the range of between 6 and 12° from the longitudinal axis C of the venturi passageway. By this nozzle member, being operatively connected with the pouch inside the container, there is provided a flow of said ophthalmic solution of 1–20 ml/10 sec, preferably 2–16 ml/10 sec, at a major droplet size of 20–400 $\mu$m, preferably 35–90 $\mu$m. A small droplet size will efficiently give a large specific rinsing surface of the spray and also the impact pressure will be low for each droplet, thus creating a comfortable spray pattern to the eye. An impact pressure of at least 0.1 g/cm$^2$ but not more than 1 g/cm$^2$ has proven to be efficient, yet comfortable to the eye.

By the bag-in-can concept, there is provided a pressurized device, adapted to give a very even and constant flow of the solution, without the use of halogenated drive gas. Moreover, the compressed drive gas, which normally consists of nitrogen gas or air, does not come in contact with the solution inside the pouch. The pouch is beneficially designed in an essentially diffusion proof multi-layer laminate, known per se and preferably comprising polypropylene (PP), oriented polyamide (OPA), aluminum (ALU) and polyethylene (PET). Advantageously, but not necessarily, the pouch is provided with longitudinal sealing edges, protruding at least 5 mm, preferably at least 7 mm, and even more preferred at least 10 mm from a filling body of the pouch. The filling body of the pouch has a lateral dimension, in its filled state, which is fairly equal or somewhat larger than a lateral dimension of said container. By the sealing edges (or flanges), the pouch is, to some extent, secured inside the container. This is the case since the protruding sealing edges will be pressed against the inner wall of the container. To further improve the securing of the pouch, in order for the connection between the mounting cup and the pouch not to let go if the container is dropped into the floor or the like, the inner surface of the container and/or the outer surface of the pouch may be provided with a friction enhancing surface.

Thanks to the device having an appearance identical to a conventional pressurized can (normally including a halogenated drive gas), there is not needed any special instructions for the use of the device. This means that any person who has received chemical or physical contamination in the eyes, may use the device directly, without hesitation about how to use it. Moreover, the ophthalmic solution will be delivered immediately, when the actuator button is being pressed down, which means that no time is lost before the eyes can be rinsed. A further major advantage is that no free space above the eyes of the individual is required for treatment, since the shower can be activated from any position.

BRIEF DESCRIPTION OF THE DRAWINGS

Having thus described the invention in general terms, reference will now be made to the accompanying drawings, which are not necessarily drawn to scale, and wherein:

FIG. 1 is a perspective view of a pouch which is integrated with a mounting cup, for mounting on the neck of the can.

FIG. 2 is a cross-sectional view of the can and pouch with a nozzle member to be used, in order to provide the desired spray flow.

FIG. 3 is a cross-sectional view of the dispensing device according to the invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

In FIG. 1 there is illustrated a pouch 1 to be accommodated inside a pressure container. The pouch comprises a bag 4, which is flat in its unfilled state, and which is formed by an essentially diffusion-proof multi-layer laminate. The volume of the bag 4 is 30–400 ml, the two most preferred volumes being 75 ml and 200 ml, respectively. At the lower end 2 of the bag, there is a folded, preferably double-folded, edge. Along the longitudinal edges of the bag 4, there are sealing edges 3, normally consisting of welded edges. According to a preferred embodiment of the invention, these sealing edges 3 exhibit a certain width, which will result in a fictional securing of the bag inside the container. At the upper end of the bag 4, there is arranged a mounting cup 5, which is sealingly connected, preferably welded, to the bag 4 at a connection member 6. In this regard, the bag should not be too big, in order for the bag 4 not to let go from the connection member 6 if the device is dropped onto the floor. The connection member 6 consist of a preferably plastic tube, accommodating a conventional non-return valve 6A (see FIG. 2) including a spring—valve body—valve seat assembly, which as is well known per se opens up when the valve body 6A is forced out of contact with the valve seat 6B, counteracting the resilient force of the spring. The exit of the connection member 6, for the ophthalmic solution contained in the bag, is a small hole 7 in the mounting cup 5. The top part of the mounting cup 5 consists of a metal cup 8, provided with a double walled circumference, below which there is arranged a gasket (not shown).

In FIG. 2 there is illustrated a cross sectional view of the portion of a container with a pouch and a preferred actuator/nozzle member 9 for the device according to the invention. The nozzle member 9 is preferably made of a plastic material and exhibits a lower connection part 10, adapted to fit the inner part of the mounting cup 5. The nozzle member 9 further comprises a centrally arranged cylindrical tube member 11, extending essentially all the way down to and through the lowermost part 10 of the nozzle member 9, and exhibiting an open end 11A at that location. The tube end 11A abuts the upper surface of the valve body 6A, which is arranged with grooves (not shown, but known per se). When the valve body 6A is moved downwardly out of contact with the seat (e.g. rubber ring) the solution in the pouch can move into the tube 11 via said grooves. The tube member 11 exhibits a bend 12, level with a nozzle outlet 13. After the bend 12, the tube member 11 extends essentially horizontally towards the nozzle outlet 13. Between the bend 12 and the outlet 13 there is arranged a kind of a screening device 14, which as is known per se can guarantee the desired flow even if any undesired particle would enter the tube 11. At the nozzle outlet 13, there is provided a venturi passageway, including a constriction which forms the smallest diameter of the tube member 11. Thereby, there is achieved a desired conical spray pattern from the nozzle outlet 13. The cylindrical tube member 11 normally exhibits a diameter of about 1–2 mm, and a smallest diameter, at the venturi passageway 13, of less than 1 mm, preferably 0.05–0.7 mm for an isotone solution of sodium chloride. Depending on the type of solution, especially depending on its viscosity, the smallest diameter of the venturi passageway is optimized together with the pressure inside the container and the volume of the bag in order to yield a spray time of normally 5–15 minutes.

Figure 2:
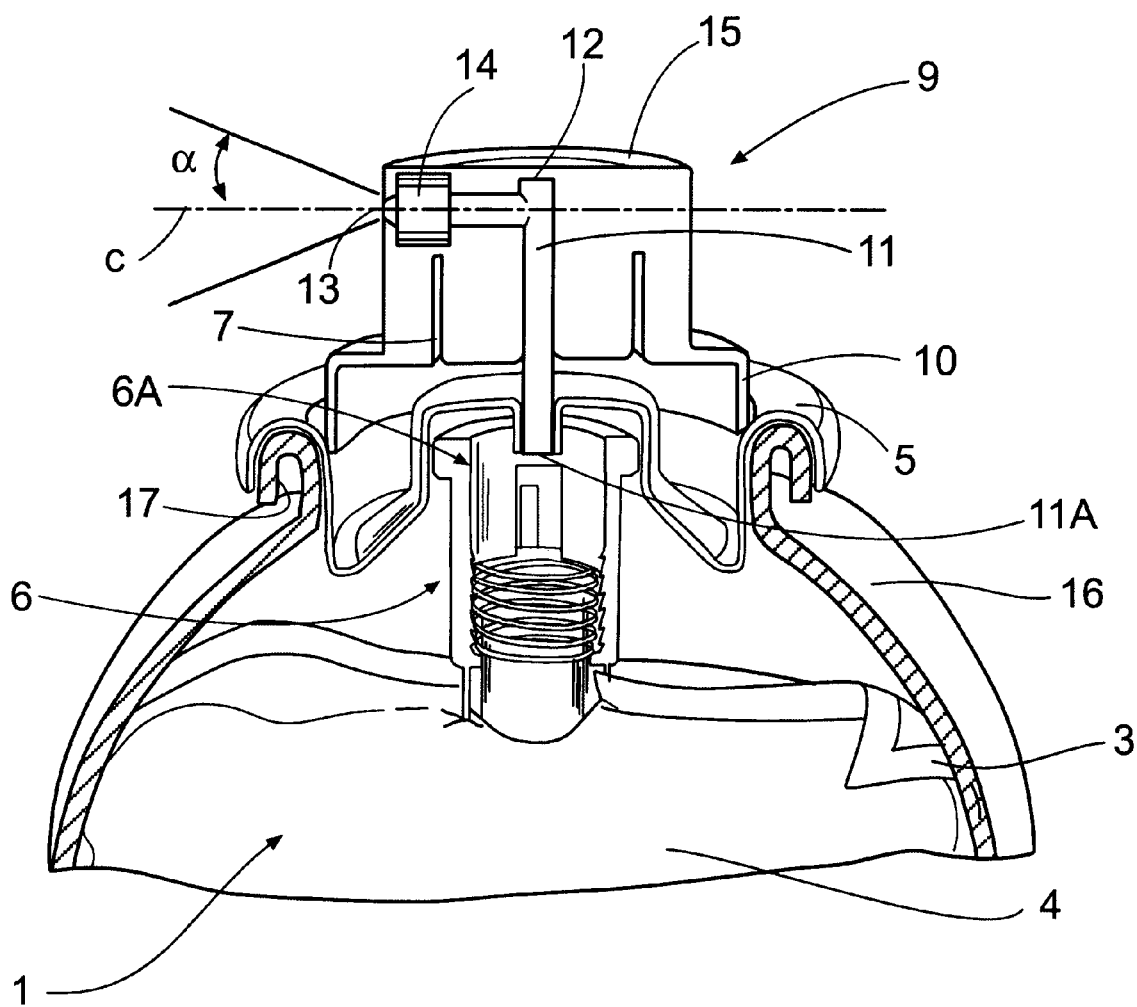

The actuator/nozzle member 9 also includes an actuator surface 15, for the pressing with a finger of an operator. FIG. 2 also shows a side view of a cylindrical pressure container (or can) 16, which preferably is made of aluminum or steel and which suitably is designed to withstand an internal pressure of at least 12 bar, preferably at least 18 bar. The volume of the container is 1 liter at the most, preferably 500 ml at the most. The two most preferred volumes are 140 ml and 335 ml, respectively. The container 16 is provided with an open top defining a reinforced neck 17 with a diameter that corresponds to a diameter of the double walled circumference of the mounting cup 5. Accordingly, as can be seen from FIG. 2, the mounting cup 5 may be arranged on the reinforced neck 17 of the container 16, with the bag/pouch 4 being arranged inside the container. Thereafter, the nozzle member 9 is arranged on the mounting cup. Preferably, there is arranged a plastic dust cap on the top of nozzle member 9 (not shown).

The pouch 1 exhibits, as has been previously described, at least two longitudinal sealing edges 3. These edges (or flanges) 3, together with the fact that the filling body of the pouch has a lateral dimension, in its filled state, which is fairly equal or somewhat larger than a lateral dimension (i.e. the diameter) of the container 16, assures that the pouch 1 is securely arranged inside the container 16. The width of the sealing edges 3 may be optimized, i.e. increased in relation to the width of conventional sealing edges, in order to further improve the securing of the pouch inside the container. Furthermore, the inner surface of the container 16 and/or the outer surface of the pouch 1 may be provided with a friction enhancing surface, such as a rugged surface.

When the actuator surface 15 of the nozzle member 9 is pressed on, this will result in the entire nozzle member being pressed down, whereby the lower end of the tube member 11 will be forced into the hole 7 of the mounting cup 5 and effect release of the valve body 6A so that a flow of ophthalmic solution will take form in the tube member 11, because of the pressure acting on the pouch 4 within the can 16.

In an alternative male-type embodiment of the nozzle member (not shown), as is well known per se, the vertical part of the tube member is formed by a separate part, which is mounted in the hole 7 of the mounting cup 5. In this case, the nozzle member 9 exhibits a larger diameter vertical receiving part for receiving the separate part of the tube member, but the outlet is designed as described above in order to produce the desired function.

Figure 3:
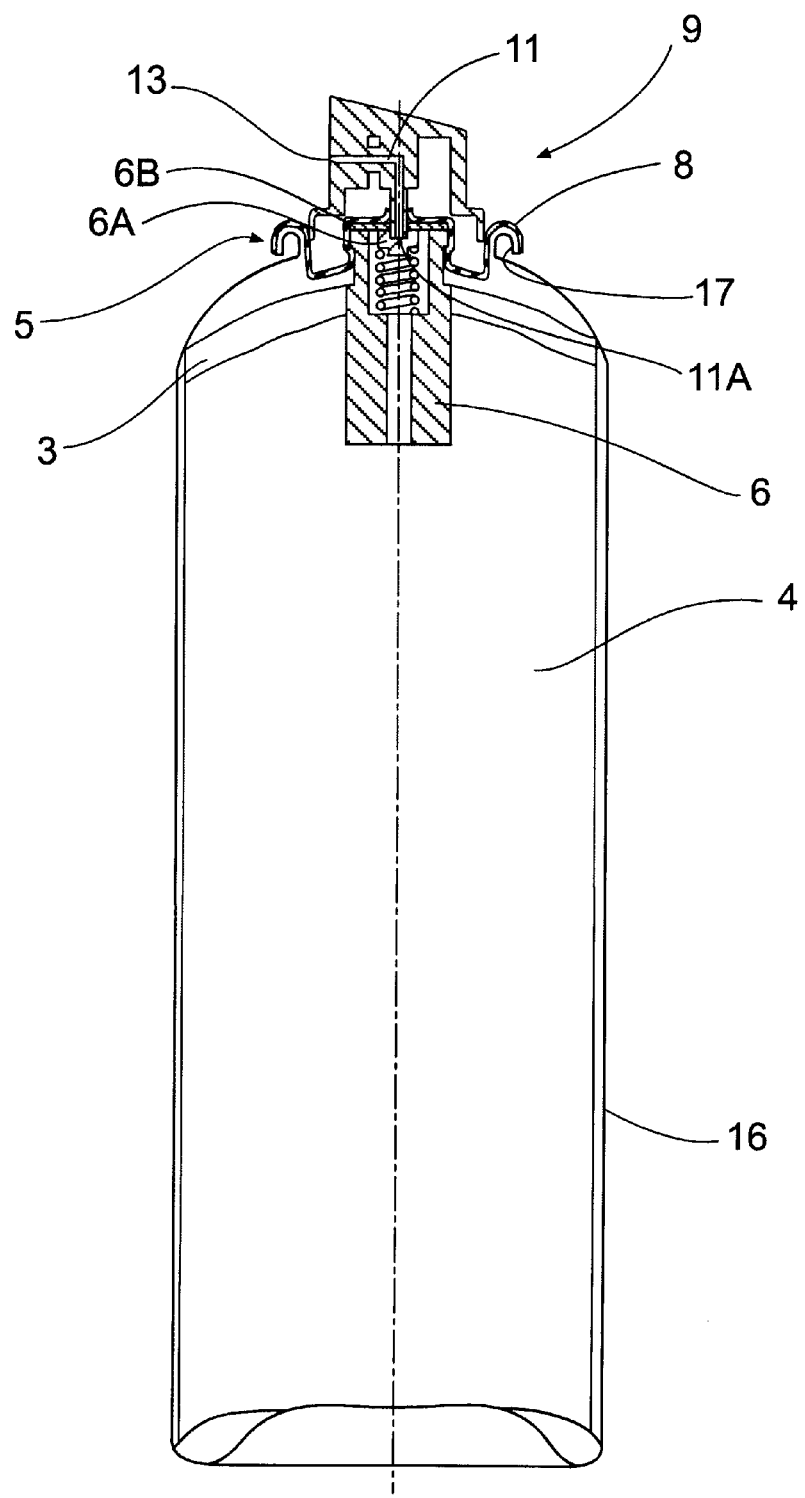

In FIG. 3 there is shown a further cross-sectional view of the dispensing device with a filled pouch 4 and, wherein the design of the valve 6 is slightly different compared to FIG. 2. Here the tube end 11A protrudes into a cavity within the valve body. The function however, is the same as described in connection with FIG. 2. It is also shown how the vertical part of the cylindrical tube member 11 in the nozzle member 9 will protrude into the hole of the mounting cup 5. Furthermore, it is shown how the double walled circumference of the mounting cup 5 will enclose the reinforced neck 17 of the container 16.

The procedure for filling the device with a pressurized gas (propellant), such as air or $N_2$, and with an ophthalmic solution, such as an isotone (0.9%) sodium chloride solution, is as follows. The container 16 is filled with the gas, via the open top of the container, to a pressure of about 2 bar. Thereafter, while retaining the pressure inside the container 16, the mounting cup 5 is mounted on the neck of the container and the double walled circumference of the mounting cup is mechanically crimped (plastic deformation) onto the reinforced neck 17 of the container 16. Now, the solution is filled into the pouch 1, through the valve in the connection member 6 of the pouch. The non-return valve is in this connection mechanically opened to allow a flow in the "wrong" direction. The pouch is filled to take about 60% of the total free volume inside the container, whereby the pressure inside the container is increased to 4–7 bar, or about 5 bar. The filling is aseptically performed, resulting in 50 CFU/ml at the most (CFU=Colony Forming Units). After the filling, the whole container is sterilized by gamma radiation, of min 25 kGrey. Finally, the nozzle member 9 and a possible dust cap is mounted on the mounting cup 5 and the device is ready for use.

In order for the pressure inside the container not to fall too quickly during use, it may be preferred to have a higher initial gas/solution ratio inside the container, whereby e.g. 45–55%, or about 50%, of the total free volume consist of gas, the rest consisting of the solution. In this embodiment it may be especially preferable to provide the pouch with extra wide sealing edges and/or to provide the inside of the container and/or the outside of the pouch with a friction enhancing surface, in order to properly secure the pouch inside the container.

In an alternative, not preferred and not shown, embodiment, the filling of the pressurized gas may take place through a separate valve in the wall of the container, after the mounting cup has been crimped onto the neck of the container. In this case, the solution may be filled into the pouch before the gas is being filled into the container. The filling ratio and the total pressures will however be the same as is described above.

The invention is not limited to the above described preferred embodiments, but may be varied within the scope of the claims. A further advantage of the device is that it may be used for wound wash as well, at least when the solution consists of an isotone sodium chloride solution.

It is also realized that the concept of the invention can be extended to other uses of the device shown herein. Certain adaptations of the nozzle member and/or of other features of the device may in that case be necessary, but nevertheless the device to be used may be essentially similar to the device shown herein, filled with some other solution. A conceivable field of use is the veterinary field, such as a spray device for iodine, for a disinfective solution such as chlorhexidine or for a liniment. Other uses within the human treatment field are also conceivable, such as a device for a nose spray, or a spray device for a saliva substitute, for a disinfective solution such as chlorhexidine, for wound wash, for personal hygiene, for a gel or solution for treatment of burn injuries, for a NaCl gel for natural skin moisturizing, for a gel or solution for local anaesthetics, such as Xylocain or for a plaque detector.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A manually operated dispensing device for dispensing an ophthalmic solution, the device being adapted to deliver the ophthalmic solution to a surface of an eye in a desired spray pattern with an impact pressure on the eye that is comfortably tolerated by an individual, the device comprising:
   a container having a neck defining an opening;
   a pressurized gas capable of being contained within the container;
   collapsible pouch configured to be contained within the container;
   an ophthalmic solution contained within the pouch;
   a mounting cup configured to operably engage the pouch so as to seal the ophthalmic solution therein, the mounting cup being further configured to sealingly engage the neck so as to retain the pouch within the container and to seal the pressurized gas between the container and the pouch such that the pressure of the pressurized gas is exerted on the pouch;
   a valve operably engaged with the mounting cup and configured to be capable of releasing a flow of the ophthalmic solution from the pouch, the flow through the valve being generated by the pressure exerted on the pouch;
   a nozzle member in communication with the valve and configured to receive the flow and direct the flow of the ophthalmic solution therefrom in a selected spray pattern; and
   an actuator operably engaged between the valve and the nozzle member for actuating the valve so as to initiate the flow from the valve through the nozzle member, the actuator being further configured to allow selective deactuation of the valve, so as to thereby selectively stop the flow of the ophthalmic solution through the nozzle member, after the valve has been actuated by the actuator.

2. A device according to claim 1 wherein the nozzle member defines a nozzle inlet in communication with the valve for receiving the flow and a nozzle outlet for dispensing the flow therefrom, the nozzle further defining a venturi passageway between the nozzle inlet and the nozzle outlet, the venturi passageway having a longitudinal axis.

3. A device according to claim 2 wherein the venturi passageway is configured to cooperate with the nozzle outlet so as to dispense the ophthalmic solution from the nozzle outlet in a conical spray pattern diverging at an angle of between about 6° and about 12° from the longitudinal axis.

4. A device according to claim 1 wherein the nozzle member is configured to regulate the flow to provide a flow rate of the ophthalmic solution of between about 0.1 ml/sec and about 2 ml/sec.

5. A device according to claim 1 wherein the nozzle member is configured to regulate the flow to provide a major droplet size of the ophthalmic solution of between about 20 $\mu$m and about 400 $\mu$m.

6. A device according to claim 1 wherein the nozzle member is configured to regulate the flow to provide an impact pressure of the ophthalmic solution of between about 0.1 g/cm$^2$ and about 1 g/cm$^2$.

7. A device according to claim 1 wherein the valve is configured as a non-return valve for preventing a backflow of the ophthalmic solution into the pouch once the ophthalmic solution is dispensed from the pouch.

8. A device according to claim 1 wherein the mounting cup is crimped about the neck of the container.

9. A device according to claim 1 wherein the container is configured to have a volume of no more than about 1 liter and is configured to contain the pressurized gas at a pressure of no more than about 10 bar.

10. A device according to claim 1 wherein the pouch containing the ophthalmic solution is configured to occupy no more than about 60% of the container such that the pressurized gas occupies at least about 40% of the container.

11. A device according to claim 1 wherein the pouch is comprised of a substantially diffusion-proof multi-layer flexible laminate material, the material being folded and then sealed along longitudinal edges thereof so as to form at least two longitudinal sealing edges and a filling body defining a filling compartment therein.

12. A device according to claim 11 wherein the longitudinal sealing edges extend at least about 5 mm from the filling body.

13. A device according to claim 11 wherein the container has an inner lateral dimension and the filling body, when the filling compartment is filled with the ophthalmic solution, has an outer lateral dimension greater than the inner lateral dimension of the container.

14. A device according to claim 1 wherein the container has an inner surface, the inner surface being configured so as to be friction enhancing for securing the pouch within the container.

15. A device according to claim 1 wherein the pouch has an outer surface, the outer surface being configured so as to be friction enhancing for securing the pouch within the container.

16. A device according to claim 1 further comprising a filling valve operably engaged with the container and configured to allow the container to be filled with the pressurized gas therethrough.

17. A device according to claim 2 wherein the venturi passageway has a diameter of no more than about 1 mm when the ophthalmic solution comprises an isotone solution of sodium chloride.

18. A method of washing at least one of an eye and a wound, said method comprising:
   actuating a manually operated dispensing device so as to dispense a solution, the device being configured to deliver the solution in a desired spray pattern with an impact pressure that is comfortably tolerable, the device comprising:
   a container having a neck defining an opening;
   a pressurized gas capable of being contained within the container;
   a collapsible pouch configured to be contained within the container;
   a solution contained within the pouch;
   a mounting cup configured to operably engage the pouch so as to seal the solution therein, the mounting cup being further configured to sealingly engage the neck so as to retain the pouch within the container and to seal the pressurized gas between the container and the pouch such that the pressure of the pressurized gas is exerted on the pouch;

a valve operably engaged with the mounting cup and configured to be capable of releasing a flow of the solution from the pouch, the flow through the valve being generated by the pressure exerted on the pouch;

a nozzle member in communication with the valve and configured to receive the flow and direct the flow of the solution therefrom in a selected spray pattern; and an actuator operably engaged between the valve and the nozzle member for actuating the valve so as to initiate the flow from the valve through the nozzle member, the actuator being further configured to allow selective deactuation of the valve; and selectively deactuating the device so as to stop the flow of the solution through the nozzle member, after the device has been actuated.

19. A method according to claim 18 further comprising sterilizing the solution in the pouch by exposing the container to gamma radiation of at least about 25 kGrey.

* * * * *

UNITED STATES PATENT AND TRADEMARK OFFICE
CERTIFICATE OF CORRECTION

PATENT NO. : 6,547,770 B2
DATED : April 15, 2003
INVENTOR(S) : Tony Carlsson and Bengt Hedman It is certified that error appears in the above-identified patent and that said Letters Patent is hereby corrected as shown below:

Column 7,
Line 22, before "collapsible" insert -- a --.

Column 8,
Line 22, "scaling" should read -- sealing --.

Signed and Sealed this

Ninth Day of September, 2003

JAMES E. ROGAN
*Director of the United States Patent and Trademark Office*